US010633602B2

United States Patent
Solomon

(10) Patent No.: US 10,633,602 B2
(45) Date of Patent: Apr. 28, 2020

(54) DISSOLUTION OF HEXAMINE IN NON-AQUEOUS SOLVENT

(71) Applicant: Ecolab USA Inc., St. Paul, MN (US)

(72) Inventor: Kim R. Solomon, River Falls, WI (US)

(73) Assignee: ECOLAB USA INC., St. Paul, MN (US)

( * ) Notice: Subject to any disclaimer, the term of this patent is extended or adjusted under 35 U.S.C. 154(b) by 103 days.

(21) Appl. No.: 15/935,370

(22) Filed: Mar. 26, 2018

(65) Prior Publication Data

US 2018/0282637 A1    Oct. 4, 2018

Related U.S. Application Data

(60) Provisional application No. 62/478,427, filed on Mar. 29, 2017.

(51) Int. Cl.

| | | |
|---|---|---|
| *C10G 29/00* | (2006.01) | |
| *C10G 29/22* | (2006.01) | |
| *C04B 26/26* | (2006.01) | |
| *C04B 41/53* | (2006.01) | |
| *C10G 29/20* | (2006.01) | |
| *C10C 3/02* | (2006.01) | |
| *B01D 53/52* | (2006.01) | |
| *C08K 5/3477* | (2006.01) | |
| *C04B 111/00* | (2006.01) | |
| *C02F 101/10* | (2006.01) | |
| *C08L 95/00* | (2006.01) | |

(52) U.S. Cl.
CPC .............. *C10G 29/22* (2013.01); *B01D 53/52* (2013.01); *C04B 26/26* (2013.01); *C04B 41/5315* (2013.01); *C08K 5/3477* (2013.01); *C10C 3/026* (2013.01); *C10G 29/20* (2013.01); *C02F 2101/101* (2013.01); *C04B 2111/00017* (2013.01); *C08L 95/00* (2013.01); *C10G 2300/207* (2013.01)

(58) Field of Classification Search
CPC .. C10G 29/20; C10G 2300/207; C04B 26/26; C04B 41/5315; C04B 2111/00017; C10C 3/026; C08K 5/3477; C08L 95/00; C02F 2101/101; B01D 53/52

See application file for complete search history.

(56) References Cited

U.S. PATENT DOCUMENTS

| | | | |
|---|---|---|---|
| 5,213,680 A | * | 5/1993 | Kremer ................. C10G 29/20 208/189 |
| 6,444,117 B1 | | 9/2002 | Khan et al. |
| 7,264,786 B2 | | 9/2007 | Pakulski et al. |
| 9,409,119 B2 | | 8/2016 | Murai et al. |
| 2005/0130847 A1 | | 6/2005 | Gatlin et al. |
| 2016/0009980 A1 | | 1/2016 | Gupta et al. |

FOREIGN PATENT DOCUMENTS

| | | |
|---|---|---|
| CN | 101889568 A | 11/2010 |
| CN | 102140364 A | 3/2011 |
| CN | 104327588 A | 2/2015 |
| RU | 2230096 C1 | 6/2004 |
| RU | 2269567 C1 | 2/2006 |
| RU | 2302523 | 7/2007 |
| RU | 2479615 | 4/2013 |
| RU | 2522459 C1 | 7/2014 |
| RU | 2577556 C1 | 3/2016 |
| UA | 85923 | 12/2013 |
| WO | WO 9301126 | 1/1993 |

OTHER PUBLICATIONS

Forno, C., "The Growth of Large Crystals of Hexamine From Solution" Journal of Crystal Growth (1974) 21: 61-64.

* cited by examiner

*Primary Examiner* — Randy Boyer
*Assistant Examiner* — Brandi M Doyle
(74) *Attorney, Agent, or Firm* — Eric D. Babych; Barnes & Thornburg LLP

(57) ABSTRACT

The present disclosure generally relates to scavenging hydrogen sulfide. The disclosure pertains to non-aqueous and non-volatile compositions that include a monolignol alcohol and hydrogen sulfide scavenging compound. The hydrogen sulfide scavenging compound may be hexamine in some aspects. The compositions may also include a $C_{2-8}$ polyol. The compositions disclosed are stable and can be used, for example, in removing hydrogen sulfide from hot asphalt.

4 Claims, No Drawings

DISSOLUTION OF HEXAMINE IN NON-AQUEOUS SOLVENT

BACKGROUND

1. Field of the Invention

The present disclosure generally relates to scavenging hydrogen sulfide. More particularly, the disclosure pertains to the use of non-aqueous hexamine compositions to scavenge hydrogen sulfide present in asphalt.

2. Description of the Related Art

Petroleum asphalt is produced as a residue of a thermal separation refinery process. The thermal separation process causes thermal cracking to occur which frequently causes hydrogen sulfide to be present in the asphalt stream. In fact, thermal cracking continues in the asphalt even after the asphalt has left the vacuum distillation section of the operation, particularly at high temperature. In order to permit the safe loading, handling, and storage of the asphalt, it is necessary to reduce the hydrogen sulfide to safe levels in the asphalt. This has been done in the past by weathering of the hot asphalt for sufficient time for the hydrogen sulfide to be reduced to safe levels. This not only takes a considerable amount of time (several days), but it releases hydrogen sulfide to the vapor space in the storage, which could create hazardous conditions. Moreover, recent emphasis on environmental regulations in Europe stresses the limits on the hydrogen sulfide content of vent gas.

BRIEF SUMMARY

In some embodiments, a composition is provided that includes a monolignol alcohol and a compound of formula (I) or formula (II)

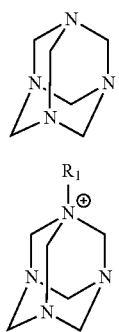

(I)

(II)

where $R_1$ may be a substituted or unsubstituted $C_{1-32}$ alkyl, a substituted or unsubstituted $C_{2-32}$ alkenyl, or a substituted or unsubstituted $C_{2-32}$ alkynyl. The substituted $C_{1-32}$ alkyl, the substituted $C_{2-32}$ alkenyl, and the substituted $C_{2-32}$ alkynyl may be substituted with hydroxyl or $C_{1-5}$ alkyl.

In some embodiments, the monolignol alcohol is selected from the group consisting of p-coumaryl alcohol, coniferyl alcohol, sinapyl alcohol, cinnamyl alcohol, and any combination thereof. The monolignol alcohol may be cinnamyl alcohol. The monolignol alcohol may be coniferyl alcohol. The compound may be hexamine.

In some embodiments, the composition comprises a $C_{2-8}$ polyol. The $C_{2-8}$ polyol may be glycerin.

In some embodiments, the composition comprises the compound of formula (I), cinnamyl alcohol, and glycerin.

In some embodiments, the composition comprises about 2 to about 20 weight percent of the compound of formula (I) or formula (II). The composition may comprise about 10 to about 98 weight percent of the monolignol alcohol. The composition may comprise about 2 to about 80 weight percent of the $C_{2-8}$ polyol.

In some embodiments, a weight ratio of the monolignol alcohol to the $C_{2-8}$ polyol is about 10:1 to about 20:1. In some embodiments, a weight ratio of the compound of formula (I) or formula (II) to monolignol alcohol is about 1:15 to about 1:1.

In some embodiments, the composition comprises an amount of water that is less than about 1% by weight. In some embodiments, the composition excludes water.

The composition may comprise a pH greater than about 7.

In some embodiments, a method is provided for scavenging hydrogen sulfide in an industrial process. The method may include adding an effective amount of a composition to a medium in the industrial process. The composition may include a monolignol alcohol and a compound of formula (I) or formula (II)

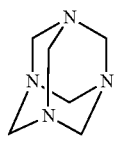

(I)

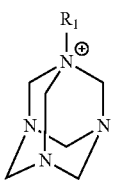

(II)

where $R_1$ is a substituted or unsubstituted $C_{1-32}$ alkyl, a substituted or unsubstituted $C_{2-32}$ alkenyl, or a substituted or unsubstituted $C_{2-32}$ alkynyl, wherein the substituted $C_{1-32}$ alkyl, the substituted $C_{2-32}$ alkenyl, and the substituted $C_{2-32}$ alkynyl are substituted with hydroxyl or $C_{1-5}$ alkyl.

In some embodiments, the composition of the method further comprises a $C_{2-8}$ polyol and the monolignol alcohol is cinnamyl alcohol.

In some embodiments, the effective amount is in a range from about 0.00001 ppm to about 100,000 ppm.

In some embodiments, the medium is selected from the group consisting of crude oil, diesel fuel, asphalt and any combination thereof.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

DETAILED DESCRIPTION

Various embodiments are described below. The relationship and functioning of the various elements of the embodiments may better be understood by reference to the following detailed description. However, embodiments are not limited to those illustrated below. In certain instances details may have been omitted that are not necessary for an understanding of embodiments disclosed herein.

Environmental standards and safety standards require the removal of hydrogen sulfide from oil, asphalt, or other materials. Various strategies and chemicals are used to remove hydrogen sulfide.

Hexamine can be used as a hydrogen sulfide scavenger. Hydrogen sulfide scavenger refers to compounds that may eliminate hydrogen sulfide or reduce its concentration in a medium such as oil, asphalt, or diesel. Hexamine decomposes in the presence of acid to ammonia and formaldehyde. Formaldehyde or ammonia can then react with hydrogen sulfide converting the volatile and toxic gas into a nonvolatile material. Despite the usefulness of hexamine, it has limited solubility in common solvents. Some solvents that can effectively dissolve hexamine are volatile and incompatible with compositions that need to be added to hot asphalt. Additionally, hexamine is available in at least two different forms. Hexamine can be in a hexahydrate form that melts below room temperature at 13° C., which is generally described as an "aqueous solution" of hexamine. Hexamine can be in a pure solid form with a melting point of about 280° C.

Hexamine has limited solubility in most common organic solvents at 20° C.: 13.4 g in chloroform, 7.25 g in methanol, 2.89 g in ethanol, 0.65 g in acetone, 0.23 g in benzene, 0.14 g in xylene, 0.06 g in ether, and near zero in petroleum ether. Chloroform is not suitable due to toxicity, and ethanol and acetone are too volatile for use in use in hot asphalt, which can be up to 300-400° F.

The present disclosure seeks to solve the problems associated with the solubility of hexamine. The compositions may be non-aqueous and non-volatile, which is ideal for applications involving hot material such as asphalt. The compositions may be halogen-free, which is desirable for improved worker safety.

In some embodiments, a composition is disclosed for scavenging hydrogen sulfide. The composition may include a hydrogen sulfide scavenger. The hydrogen sulfide scavenger may be a compound of formula (I) or formula (II) as shown below,

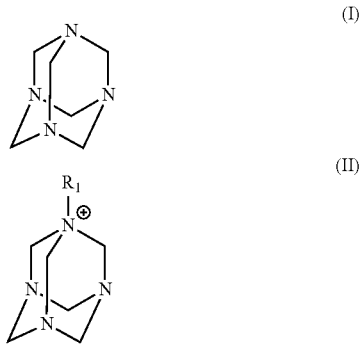

where $R_1$ may be a substituted or unsubstituted $C_{1-32}$ alkyl, a substituted or unsubstituted $C_{2-32}$ alkenyl, or a substituted or unsubstituted $C_{2-32}$ alkynyl. The substituted $C_{1-32}$ alkyl, substituted $C_{2-32}$ alkenyl, and substituted $C_{2-32}$ alkynyl may be substituted with a hydroxyl group or a $C_{1-5}$ alkyl.

In some embodiments, $R_1$ may be a substituted or unsubstituted $C_{1-8}$ alkyl, a substituted or unsubstituted $C_{2-8}$ alkenyl, or a substituted or unsubstituted $C_{2-8}$ alkynyl. The substituted $C_{1-8}$ alkyl, substituted $C_{2-8}$ alkenyl, and substituted $C_{2-8}$ alkynyl may be substituted with a hydroxyl group or a $C_{1-5}$ alkyl.

The term "alkyl," as used herein, refers to a linear or branched hydrocarbon radical, preferably having 1 to 32 carbon atoms (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons). Examples of unsubstituted alkyl groups include methyl, ethyl, n-propyl, i-propyl, n-butyl, i-butyl, s-butyl, t-butyl, n-pentyl, i-pentyl, s-pentyl, t-pentyl, and the like.

The term "alkenyl," as used herein, refers to a straight or branched hydrocarbon radical, preferably having 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons, and having one or more carbon-carbon double bonds. Alkenyl groups include, but are not limited to, ethenyl, 1-propenyl, 2-propenyl (allyl), iso-propenyl, 2-methyl-1-propenyl, 1-butenyl, and 2-butenyl.

The term "alkynyl," as used herein, refers to a straight or branched hydrocarbon radical, preferably having 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons, and having one or more carbon-carbon triple bonds. Alkynyl groups include, but are not limited to, ethynyl, propynyl, and butynyl.

In some embodiments, the compound of formula (I) may be hexamine, which is also known as hexamethylenetetramine, methenamine, urotropine, or 1,3,5,7-tetraazatricyclo[3.3.1.1$^{3,7}$]decane. Hexamine is readily available from common chemical suppliers.

The composition may also include a monolignol alcohol. Monolignol alcohols may be isolated from various species of plants and trees. The monolignol alcohol may be p-coumaryl alcohol, coniferyl alcohol, sinapyl alcohol, or cinnamyl alcohol.

In certain embodiments, the composition may have about 2 to about 20 weight percent of the compound of formula (I) or formula (II). The amount of the compound of formula (I) or formula (II) in the composition may range from about 5 to about 20 weight percent, about 5 to about 15 weight percent, or about 7 to about 12 weight percent. In some embodiments, the amount of the compound of formula (I) or formula (II) may be about 7 weight percent, 8 weight percent, about 9 weight percent, about 10 weight percent, about 11 weight percent, about 12 weight percent, about 13 weight percent, about 14 weight percent, or about 15 weight percent.

Monolignol alcohols originates from certain plants, such as grass, and can be purchased from chemical suppliers at varying degrees of purity. The monolignol alcohol in the composition may include a mixture of one or more of p-coumaryl alcohol, coniferyl alcohol, sinapyl alcohol, or cinnamyl alcohol, including any other monolignol alcohols.

In other embodiments, the monolignol alcohol may be p-coumaryl alcohol.

In some embodiments, the monolignol alcohol may be coniferyl alcohol.

In some embodiments, the monolignol alcohol may be sinapyl alcohol.

In some embodiments, the monolignol alcohol may be cinnamyl alcohol.

In certain embodiments, the monolignol alcohol may be a mixture of one or more of p-coumaryl alcohol, coniferyl alcohol, sinapyl alcohol, or cinnamyl alcohol.

In some embodiments, the composition may consist of the compound of formula (I) or formula (II) and a monolignol alcohol. The composition may consist of the compound of formula (I) and cinnamyl alcohol. The composition may consist of hexamine and cinnamyl alcohol.

In some embodiments, the composition may have about 10 to about 98 weight percent of the monolignol alcohol. In other embodiments, the monolignol alcohol present in the composition may range from about 20 to about 98 weight percent, about 30 to about 98 weight percent, about 40 to about 98 weight percent, about 50 to about 98 weight percent, about 60 to about 98 weight percent, about 70 to about 98 weight percent, and about 80 to about 98 weight percent.

In other embodiments, the composition may include a $C_{2-8}$ polyol. A polyol may be defined as an alcohol having multiple hydroxyl groups. In some embodiments, the composition may include a $C_{3-8}$ polyol, a $C_{4-8}$ polyol, or a $C_{5-8}$ polyol. The composition may include a $C_3$ polyol.

In some embodiments, the $C_{2-8}$ polyol may be glycerin. Glycerin is hydroscopic and may contain water. Water content in commercially available glycerin can be as low as about 1% by weight or less. In some embodiments, the composition may include an amount of water that is less than about 1% by weight. The glycerin may be prepared such that all the water may be removed by using molecular sieves, for example. In certain embodiments, the composition may exclude water.

In some embodiments, the composition may have about 2 to about 80 weight percent of the $C_{2-8}$ polyol. The amount of $C_{2-8}$ polyol in the composition may range from about 2 to about 70 weight percent, about 2 to about 60 weight percent, about 2 to about 50 weight percent, about 2 to about 40 weight percent, about 2 to about 30 weight percent, or about 2 to about 25 weight percent.

In some embodiments, the composition may include the compound of formula (I) or formula (II), cinnamyl alcohol, and a $C_{2-8}$ polyol. The composition may include the compound of formula (I) or formula (II), cinnamyl alcohol, and glycerin. In other embodiments, the composition may consist of the compound of formula (I) or formula (II), cinnamyl alcohol, and a $C_{2-8}$ polyol. The composition may consist of hexamine, cinnamyl alcohol, and glycerin.

In some embodiments, the weight ratio of the monolignol alcohol to the $C_{2-8}$ polyol may be about 10:1 to about 20:1, about 1:2 to about 20:1, about 1:1 to about 20:1, or about 1:10 to about 10:1. In certain embodiments, the weight ratio of the monolignol alcohol to the $C_{2-8}$ polyol may be about 15:1.

In some embodiments, the weight ratio of the compound of formula (I) or formula (II) to monolignol alcohol may range from about 1:20 to about 1:1. In other embodiments the weight ratio may range from about 1:15 to about 1:1, about 1:15 to about 1:2, or about 1:15 to about 1:5. In some embodiments, the weight ratio of the compound of formula (I) or formula (II) to monolignol alcohol may be about 1:8.

In some embodiments, the composition may have a pH greater than about 7. The composition may have a pH of about 7 to about 9. Generally, it may be desirable to maintain the pH at neutral or alkaline conditions before adding to the asphalt to avoid acid hydrolysis of hexamine.

In some embodiments, a method is provided for scavenging hydrogen sulfide in an industrial process. The method may include adding an effective amount of a composition to a medium in the industrial process. The composition may include a monolignol alcohol and a compound of formula (I) or formula (II)

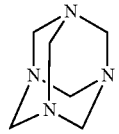

(I)

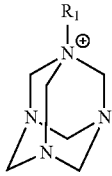

(II)

where $R_1$ is a substituted or unsubstituted $C_{1-32}$ alkyl, a substituted or unsubstituted $C_{2-32}$ alkenyl, or a substituted or unsubstituted $C_{2-32}$ alkynyl, wherein the substituted $C_{1-32}$ alkyl, the substituted $C_{2-32}$ alkenyl, and the substituted $C_{2-32}$ alkynyl are substituted with hydroxyl or $C_{1-5}$ alkyl In some embodiments, $R_1$ may be a substituted or unsubstituted $C_{1-8}$ alkyl, a substituted or unsubstituted $C_{2-8}$ alkenyl, or a substituted or unsubstituted $C_{2-8}$ alkynyl, wherein the substituted $C_{1-8}$ alkyl, the substituted $C_{2-8}$ alkenyl, and the substituted $C_{2-8}$ alkynyl may be substituted with hydroxyl or $C_{1-5}$ alkyl.

The effective amount added to the medium in an industrial process can be readily determined by one of ordinary skill in the art. An effective amount would depend at least partially on the medium's hydrogen sulfide content. Generally, if a medium contains high levels of hydrogen sulfide then more of the composition may be required. In some embodiments, the effective amount may be in a range from about 0.00001 ppm to about 100,000 ppm.

The industrial process may utilize or process crude oil, diesel fuel, asphalt or the like. The composition may be added to a medium in the industrial process, such as crude oil, diesel fuel, asphalt, or combinations thereof in order to remove unwanted hydrogen sulfide.

The composition may be added to the process continuously or dosed intermittently. A programmed logic controller may control the addition of the composition to the process. The method may include sensors that detect levels of hydrogen sulfide. The sensors may be in communication with the PLC. Once levels of hydrogen sulfide approach or reach a predetermined threshold the composition may be added to process.

The compositions and methods disclosed herein may be especially useful for removing hydrogen sulfide from hot asphalt where the use of aqueous or volatile solvents presents safety or toxicity concerns.

EXAMPLES

Example 1 Dissolution of Hexamine in Cinnamyl Alcohol and Glycerin

Slurries were prepared by mixing hexamine in cinnamyl alcohol or a mixture of cinnamyl alcohol and glycerin at about room temperature. The compositions were then allowed to sit undisturbed for two days and the clear supernatant decanted off and analyzed for composition. As the results below illustrate, clear stable solutions of hexamine in various ratios of glycerin and cinnamyl alcohol were obtained.

TABLE 1

Composition of Stable Solutions by Weight %

| Hexamine | Cinnamyl Alcohol | Glycerin (<1% water) |
|---|---|---|
| 7 | 93 | 0 |
| 10 | 84 | 6 |
| 11 | 78 | 11 |
| 10 | 68 | 22 |
| 7 | 59 | 34 |
| 7 | 50 | 43 |
| 8 | 37 | 55 |
| 5 | 32 | 63 |
| 8 | 16 | 76 |

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a compound" is intended to include "at least one compound" or "one or more compounds."

Any composition disclosed herein may comprise, consist of, or consist essentially of any of the compounds/components disclosed herein. In accordance with the present disclosure, the phrases "consist essentially of," "consists essentially of," "consisting essentially of," and the like, limit the scope of a claim to the specified materials or steps and those materials or steps that do not materially affect the basic and novel characteristic(s) of the claimed invention.

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A method for scavenging hydrogen sulfide in an industrial process, comprising:
adding an effective amount of a composition to a medium in the industrial process, wherein the composition comprises a monolignol alcohol and a compound of formula (I) or formula (II)

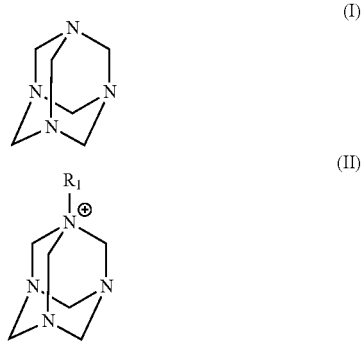

where $R_1$ is a substituted or unsubstituted $C_{1-8}$ alkyl, a substituted or unsubstituted $C_{2-8}$ alkenyl, or a substituted or unsubstituted $C_{2-8}$ alkynyl, wherein the substituted $C_{1-8}$ alkyl, the substituted $C_{2-8}$ alkenyl, and the substituted $C_{2-8}$ alkynyl are substituted with hydroxyl or $C_{1-5}$ alkyl.

2. The method of claim 1, further comprising a $C_{2-8}$ polyol, and wherein the monolignol alcohol is cinnamyl alcohol.

3. The method of claim 1, wherein the effective amount is in a range from about 0.00001 ppm to about 100,000 ppm.

4. The method of claim 1, wherein the medium is selected from the group consisting of crude oil, diesel fuel, asphalt and any combination thereof.

* * * * *

UNITED STATES PATENT AND TRADEMARK OFFICE
CERTIFICATE OF CORRECTION

| | |
|---|---|
| PATENT NO. | : 10,633,602 B2 |
| APPLICATION NO. | : 15/935370 |
| DATED | : April 28, 2020 |
| INVENTOR(S) | : Kim R. Solomon |

It is certified that error appears in the above-identified patent and that said Letters Patent is hereby corrected as shown below:

On the Title Page

In the title at item (54) and in the Specification, In Column 1, Lines 1-2, please delete "DISSOLUTION OF HEXAMINE IN NON-AQUEOUS SOLVENT" and insert --DISSOLUTION OF HEXAMINE IN NON-AQUEOUS SOLVENT MIXTURE--, therefor.

Signed and Sealed this
Twenty-fifth Day of August, 2020

Andrei Iancu
*Director of the United States Patent and Trademark Office*